(12) United States Patent
Dackson

(10) Patent No.: US 11,401,251 B2
(45) Date of Patent: Aug. 2, 2022

(54) MEMBRANE SEPARATION SYSTEM, AND USES THEREOF

(71) Applicant: Novomer, Inc., Rochester, NY (US)

(72) Inventor: Keith Dackson, East Aurora, NY (US)

(73) Assignee: Novomer, Inc., Rochester, NY (US)

( * ) Notice: Subject to any disclaimer, the term of this patent is extended or adjusted under 35 U.S.C. 154(b) by 0 days.

(21) Appl. No.: 17/437,206

(22) PCT Filed: Mar. 9, 2020

(86) PCT No.: PCT/US2020/021700
§ 371 (c)(1),
(2) Date: Sep. 8, 2021

(87) PCT Pub. No.: WO2020/190556
PCT Pub. Date: Sep. 24, 2020

(65) Prior Publication Data
US 2022/0089556 A1      Mar. 24, 2022

Related U.S. Application Data

(60) Provisional application No. 62/819,828, filed on Mar. 18, 2019.

(51) Int. Cl.
*B01D 53/22* (2006.01)
*C07D 305/12* (2006.01)
*B01D 61/24* (2006.01)
*B01D 63/02* (2006.01)
*B01D 63/08* (2006.01)

(52) U.S. Cl.
CPC ......... *C07D 305/12* (2013.01); *B01D 61/246* (2013.01); *B01D 63/02* (2013.01); *B01D 63/082* (2013.01); *B01D 2311/13* (2013.01); *B01D 2311/16* (2013.01)

(58) Field of Classification Search
CPC .... B01D 63/082; B01D 63/02; B01D 61/246; B01D 2311/16; B01D 2311/13; C07D 305/12
See application file for complete search history.

(56) References Cited

U.S. PATENT DOCUMENTS

| | | | |
|---|---|---|---|
| 4,581,236 A | 4/1986 | Bandel et al. | |
| 5,484,881 A * | 1/1996 | Gruber | A61L 15/26 528/354 |
| 6,005,068 A * | 12/1999 | Gruber | A61L 15/26 428/411.1 |
| 2005/0215713 A1* | 9/2005 | Hessell | C08G 59/24 525/162 |
| 2006/0141156 A1* | 6/2006 | Viel | C25D 15/00 427/258 |

(Continued)

OTHER PUBLICATIONS

International Search Report for Application No. PCT/US2020/021700, dated May 29, 2020.

*Primary Examiner* — Anthony R Shumate
(74) *Attorney, Agent, or Firm* — Young Basile Hanlon & MacFarlane, P.C.

(57) ABSTRACT

Provided herein are membrane separation systems and methods suitable for use in separating carbonylation catalyst from a beta-lactone product stream. Such membrane separation systems utilize a cross flow separation technique and employ a sweep stream.

11 Claims, 5 Drawing Sheets

(56) References Cited

U.S. PATENT DOCUMENTS

| | | | |
|---|---|---|---|
| 2011/0046422 A1* | 2/2011 | Mcauliffe | C07C 9/14 |
| | | | 585/16 |
| 2011/0102528 A1* | 5/2011 | Tsuchimura | G03F 7/0392 |
| | | | 347/102 |
| 2011/0262347 A1* | 10/2011 | Ruoslahti | B82Y 5/00 |
| | | | 424/1.11 |
| 2014/0275684 A1* | 9/2014 | Bielawski | B01J 21/185 |
| | | | 585/653 |
| 2016/0060386 A1* | 3/2016 | Medoff | A61Q 19/00 |
| | | | 524/599 |
| 2017/0027168 A1* | 2/2017 | Heath | A61P 17/00 |
| 2018/0030015 A1* | 2/2018 | Farmer | B01J 31/00 |
| 2018/0340174 A1* | 11/2018 | Lundorf | C12N 15/1034 |
| 2020/0190142 A1* | 6/2020 | Pang | C07K 7/06 |

* cited by examiner

MEMBRANE SEPARATION SYSTEM, AND USES THEREOF

CROSS REFERENCE TO RELATED APPLICATIONS

This application is a national stage application of PCT Application No. PCT/US2020/02100, filed Mar. 9, 2020, which claims priority to of U.S. Application No. 62/819,828, filed Mar. 18, 2019, both of which are incorporated by reference in their entireties for all purposes.

FIELD

The present disclosure relates generally to membrane separation systems and methods, and more specifically to membrane separation systems and methods that are suitable for use in separating beta-lactone from carbonylation catalyst present in a product stream obtained from carbonylation of epoxide.

BACKGROUND

Beta-lactones may be produced by combining epoxides and carbon monoxide in the presence of carbonylation catalyst. See e.g., U.S. Pat. Nos. 9,156,803; 9,096,510; and 9,403,788. For example, as described in US 2016/0288057 or EP1931472, membranes can be used to separate the carbonylation catalyst from the beta-lactone product stream. The current membrane technology generally treats the separation as a filter. Small solutes and particulates from the feed stream are extracted. The permeate typically includes solvent from the feed and solutes/particles small enough to pass through the membrane. The retentate typically includes materials too large to pass through the membrane, which includes the carbonylation catalyst.

However, carbon monoxide can present several challenges for such membranes when used on a commercial scale. For example, carbon monoxide can affect the quality of the membrane over time. The carbonylation catalysts in the feed stream and retentate stream can also become unstable and deactivated at low partial pressures of carbon monoxide, which may occur if carbon monoxide crosses the membrane and moves into the permeate stream.

Thus, what is desired in the art are alternative membrane separation technologies that can effectively separate carbonylation catalyst from the beta-lactone product stream, while maintaining the life of the membrane.

BRIEF SUMMARY

In some aspects, provided herein are membrane separation systems and methods that introduce as a sweep stream to minimize flux across the membrane of one or more components from a feed stream. The sweep stream is saturated with such one or more components in order to control flux across the membrane.

In some embodiments, such systems and methods are suitable for use in separating a carbonylation catalyst from a beta-lactone product stream obtained from the carbonylation of epoxides. The separation systems and methods described herein allow for the separation of the carbonylation catalyst in such a way as to maximize membrane reusability, stabilize catalyst and/or product, and maintain the viscosity of the retentate as it passes along the membrane. The latter benefit can further help reduce or avoid high rates of pump-head loss and of membrane fouling, which can be costly and time-consuming in commercial production.

In some aspects, provided is a membrane separation system to separate one or more components of feed stream. In some variations, the feed stream comprises beta-lactone, epoxide, carbon monoxide, carbonylation catalyst, and solvent. In one variation, the feed stream is provided from a carbonylation reaction vessel, where epoxide undergoes carbonylation in the presence of carbonylation catalyst and reaction solvent to produce beta-lactone. The product stream of the carbonylation reaction is the feed stream that is contacted with the membrane separation system.

In some embodiments, the membrane separation system comprises a membrane, which has a permeate side and a retentate side. In some embodiments, the membrane separation system receives a feed stream on the retentate side of the membrane, and receives a sweep stream on the permeate side of the membrane.

In some variations, the sweep stream is saturated with one or more components of the feed stream, and serves to minimize flux of the one or more components across the membrane. In one variation, the one or more component is carbon monoxide. Thus, in one variation, the sweep stream is saturated with carbon monoxide, and serves to minimize flux of carbon monoxide across the membrane.

The membrane separation system also outputs a permeate stream on the permeate side of the membrane. The permeate stream is formed when at least a portion of the feed stream crosses the membrane and joins with the sweep stream. In some variations, the permeate stream comprises beta-lactone.

The membrane separation system also retains a retentate stream on the retentate side of the membrane, wherein the retentate stream is formed from the remaining feed stream after at least a portion of the feed stream crosses the membrane, wherein the retentate stream comprises carbonylation catalyst, carbon monoxide, or both. In other embodiments, the retentate stream may be directed to a carbonylation reaction vessel, or recycled into the carbonylation reaction vessel from which the feed stream was provided.

In certain aspects, provided is a beta-lactone production system, comprising: a carbonylation system; and any of the membrane separation systems described herein. In some embodiments, the carbonylation system comprises: an epoxide source, configured to output epoxide; a carbon monoxide source, configured to output carbon monoxide; a carbonylation reaction vessel that (i) receives epoxide from the epoxide source, and carbon monoxide from the carbon monoxide source; (ii) produces a product stream in the presence of carbonylation catalyst and reaction solvent, wherein the product stream comprises beta-lactone, residual epoxide, residual carbon monoxide, carbonylation catalyst, and the reaction solvent; and (iii) outputs the product stream.

In some aspects, provided is a method for separating components in a feed stream using any of the membrane separation systems described herein. In some embodiments, the method comprises: contacting the membrane separation system with the feed stream on the retentate side of the membrane; contacting the membrane separation system with a sweep stream on the permeate side of the membrane, wherein the sweep stream is saturated with one or more components of the feed stream, whereby the sweep stream minimizes flux of the one or more components across the membrane; outputting a permeate stream on the permeate side of the membrane, wherein the permeate stream is formed when at least a portion of the feed stream crosses the membrane and joins with the sweep stream, wherein the permeate stream comprises beta-lactone; and retaining a retentate stream on the retentate side of the membrane, wherein the retentate stream is formed from the remaining feed stream after at least a portion of the feed stream crosses the membrane, wherein the retentate stream comprises carbonylation catalyst, carbon monoxide, or both. In certain aspects, provided is a carbonylation method to produce beta-lactone from epoxide, in which the method also includes separating one or more components of the product stream from the carbonylation reaction. In one aspect, the method also includes separating beta-lactone from carbonylation catalyst in the product stream from the carbonylation reaction.

In some variations of the foregoing methods and systems, the membrane separation system is a plate-and-frame membrane system, a hollow fiber membrane system, or a spiral membrane system.

DESCRIPTION OF THE FIGURES

The present application can be best understood by reference to the following description taken in conjunction with the accompanying figures included in the specification.

DETAILED DESCRIPTION

Figure 1:
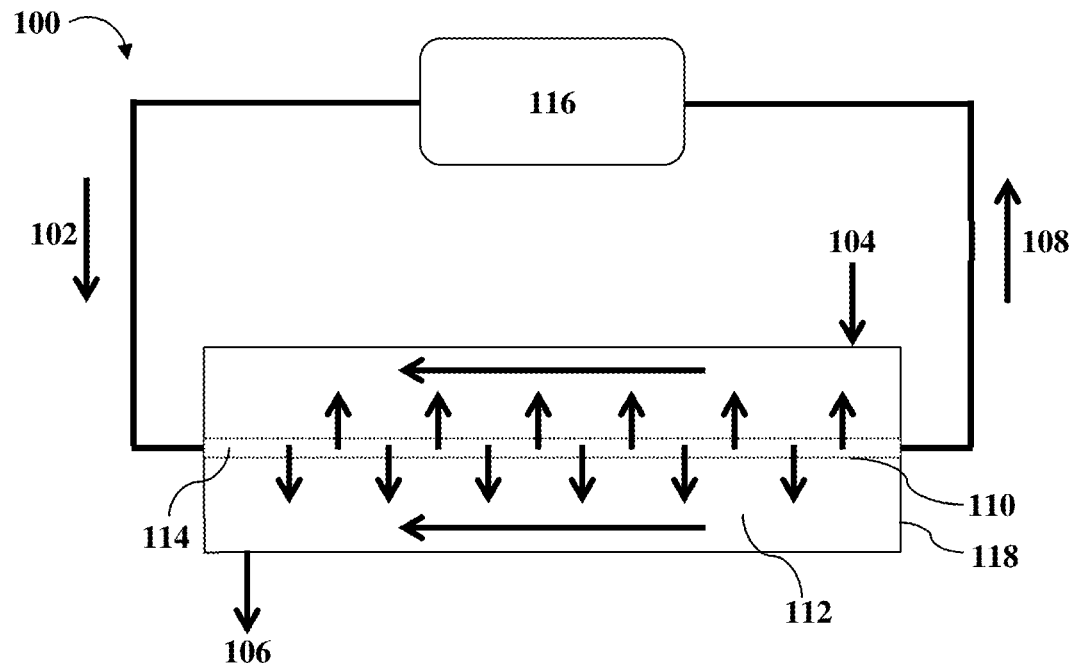
FIGS. 1, 2 and 3 depict exemplary membrane separation systems.

The following description sets forth exemplary methods, parameters and the like. It should be recognized, however, that such description is not intended as a limitation on the scope of the present disclosure but is instead provided as a description of exemplary embodiments.

Provided herein are membrane separation systems and methods that can be used to separate a specific solute or solutes from a mixture of compounds, including catalyst, raw materials and products. Such membrane separation systems and methods introduce a sweep stream saturated with one or more components of a feed stream, and such sweep stream minimizes flux of the one or more components across the membrane.

In the context of beta-lactone production from carbonylation of epoxides, the membrane separation systems and methods provided herein may be used to separate beta-lactone from carbonylation catalyst, while minimizing the flux of carbon monoxide across the membrane. For example, the carbon monoxide may be substantially prevented or minimized from crossing the membrane (e.g., about 5 percent or less, or about 1 percent or less by weight may cross the membrane). To achieve this, in some embodiments, the membrane separation system introduces a sweep stream saturated with carbon monoxide at a pressure that is approximately the same, or slightly lower, the pressure of the feed stream (e.g., the partial pressure of the carbon monoxide). This negates the need for a step to remove carbon monoxide from the feed stream prior to contact with the membrane, and can help to maintain the flow characteristics of the retentate stream. The species permeating the membrane include beta-lactone, as well as solvent and other small molecule raw materials, such as the epoxide from the carbonylation reaction. The driving force across the membrane is pressure/concentration driven diffusion.

Such a membrane separation system may be used in place of flash-membrane systems used to remove carbon monoxide from the feed stream, prior to contact with the membrane. Such membrane separation systems have the advantage of maintaining catalyst activity and system temperature, as well as reducing capital expenditures by eliminating the flash step with the associated condenser used to separate condensables from the flash stream.

Generally, the membrane separation systems described herein use a cross flow separation technique. This technique involves passing a feed stream tangentially along the surface of a membrane, on the retentate side of the membrane. The sweep stream may be a counter-current stream and the feed stream may pass tangentially along the surface of the membrane. The existence of a concentration gradient between the permeate and retentate sides of the membrane can drive certain components that are smaller than the membrane pores from the feed stream (on the retentate side) through the membrane and onto the permeate side of the membrane. Certain components that are larger than the membrane pores are retained on the retentate side and pass along the membrane surface to form the retentate stream. The carbonylation catalyst, the carbon monoxide, or both may be retained on the retentate side of the membrane.

The membrane separation systems and components therein, including the membrane, as well as the streams in contact with and output from the membrane, are described in further detail below. Moreover, the uses of such membrane separation systems in beta-lactone production systems are also described below.

The membrane separation systems comprise a membrane, or a plurality of sheets of membrane. In some embodiments, the membrane(s) may be held in place using a membrane holder. A membrane has a permeate side, which is the side of the membrane where the material that passes through the membrane goes. The membrane also has a retentate side, which is the side of the membrane where the material that does not pass through the membrane remains.

In some embodiments, the membrane separation system receives a feed stream on the retentate side of the membrane, and a sweep stream on the permeate side of the membrane. The sweep stream is saturated with one or more components of the feed stream, and helps to minimize flux (e.g., movement) of the one or more components across the membrane.

The membrane separation system outputs a permeate stream on the permeate side of the membrane. The permeate stream is formed when at least a portion of the feed stream crosses the membrane and joins with the sweep stream. The membrane separation system retains a retentate stream on the retentate side of the membrane. The retentate stream is formed from the remaining feed stream after at least a portion of the feed stream crosses the membrane.

In some variations, the membrane separation system is used in the context of a beta-lactone production system, to separate beta-lactone from carbonylation catalyst. Thus, in such variations, the feed stream comprises beta-lactone, epoxide, carbon monoxide, carbonylation catalyst, and solvent. To minimize flux of carbon monoxide across the membrane, in some variations, the sweep stream is saturated with carbon monoxide. In such variations, the permeate stream comprises at least beta-lactone; and the retentate stream comprises at least carbonylation catalyst.

With reference to FIG. 1, system 100 is an exemplary a membrane separation system. Membrane 110 is held in place by membrane holder 118. Membrane 110 has permeate side 112 and retentate side 114. Membrane 110 receives feed stream 102 on retentate side 114, and receives sweep stream 104 on permeate side 112.

System 100 may be used, in one variation, to separate components from a carbonylation product stream. It should be understood that, in such variation, the carbonylation product stream becomes the feed stream that comes in contact with the membrane separation system. For example, the feed stream may include beta-lactone, carbonylation catalyst, epoxide, carbon monoxide and carbonylation reaction solvent. System 100 may be configured to separate carbonylation catalyst from beta-lactone, while minimizing the flux of carbon monoxide across the membrane.

In some variations, membrane 110 receives feed stream 102 at a feed stream pressure and sweep stream 104 at a sweep stream pressure, such that the sweep stream pressure is equal to or lower than the feed stream pressure. Preferably, the partial pressure of the carbon monoxide on the feed side (e.g., retentate side) is equal to or less than the partial pressure of the carbon monoxide on the sweep side (e.g., permeate side) so that carbon monoxide is retained on the retentate side and does not pass through the membrane. This can create a pressure gradient that drives molecules (smaller than the membrane pores) across the membrane. The transmembrane pressure is the pressure difference between the pressure of the retentate stream (high) and pressure of the permeate stream (low). In one variation, the transmembrane pressure is between 30 bar and 40 bar. The transmembrane pressure may be between 45 bar and 60 bar. The transmembrane pressure may be equal to the feed pressure or the retentate pressure minus the permeate pressure (i.e., PT=P1−P2).

In other variations, the concentration of beta-lactone in feed stream 102 is higher than the concentration of beta-lactone in sweep stream 104. A concentration of beta-lactone in a feed stream relative to a sweep stream may drive flex of beta-lactone from the feed stream to the permeate stream. In still other variations, the concentration of beta-lactone in sweep stream 104 is zero (e.g., at start up there may be no beta-lactone in the sweep stream). Preferably, the concentration of beta-lactone in the sweep stream is greater than zero. In either case, the concentration gradient between retentate side 114 and permeate side 112 drives flux of beta-lactone from the feed stream to the permeate stream.

Components of feed stream 102 that are larger than the membrane pores will not cross membrane 110 (e.g., a molecular weight cut-off or MWCO). Components of feed stream 102 that are smaller than the membrane pores may cross membrane 110 by pressure/concentration driven diffusion. For example, carbonylation catalyst may be larger than the membrane pores, and thus will remain on the retentate side of the membrane, and be part of the retentate stream. Beta-lactone may be smaller than the membrane pores, and may cross the membrane by pressure/concentration driven diffusion, and will be part of the permeate stream.

Permeate stream 106 forms when at least a portion of feed stream 102 crosses membrane 110, and joins with sweep stream 104. Permeate stream exits on permeate side 112. Retentate stream 108 forms from remaining feed stream 102 after at least a portion of feed stream 102 crosses membrane 110. Retentate stream 108 exits on retentate side 114 of the membrane.

In certain embodiments, retentate stream 108 returns to feed reservoir 116. In certain embodiments, retentate stream 108 is continuously fed back through the membrane such that it passes over membrane 110 multiple times (e.g., in a nanofiltration system). In some variations, feed reservoir 116 is a carbonylation reaction vessel. In other variations, feed reservoir 116 is a tank that holds retentate stream 108 until it is passed along membrane 110 again.

It should be understood that, in other variations of system 100, one or more components of the system may be omitted, or additional components may be added. For example, in some variations, no feed reservoir is connected to the membrane separation system, and the membrane separation system is used in a batch process.

Figure 2:
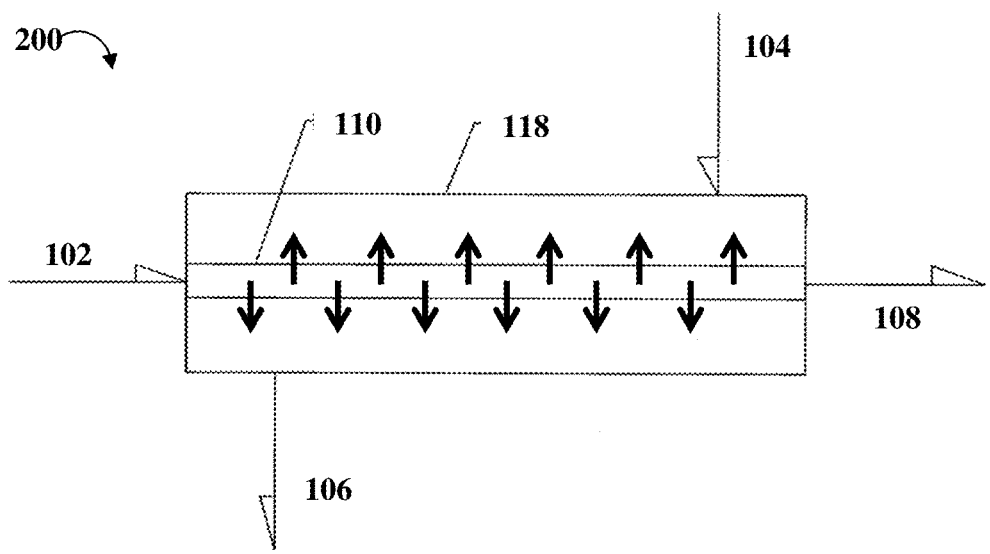

With reference to FIG. 2, system 200 is another exemplary a membrane separation system, and is a variation of system 100 discussed above. System 200 shares some of the same basic features and streams as system 100, including membrane 110, membrane holder 118, as well as feed stream 102, sweep stream 104, permeate stream 106, and retentate stream 108. Like system 100, system 200 also separates components in the feed stream by pressure/concentration driven diffusion.

System 200 may be used in batch processes. In some embodiments of system 200, permeate stream 106 and retentate stream 108 may be stored and/or directed to the next processing unit. For example, in one variation, in the context of beta-lactone production, permeate stream 106 comprises at least beta-lactone, and may be directed to a polypropiolactone production system or an acrylic acid production system. In another variation, permeate stream 106 may comprise beta-lactone, as well as epoxide and carbonylation reaction solvent, and may be directed to a further processing unit to remove the epoxide and/or carbonylation reaction solvent. The permeate stream may include reaction solvent, carbon monoxide, epoxide, or a combination thereof. The retentate stream may comprise reaction solvent, carbon monoxide, epoxide, beta-lactone, or a combination thereof. In other embodiments of system 200, retentate stream 108 comprises at least carbonylation catalyst, and may be stored or directed to a further processing system. In one variation, retentate stream 108 may comprise carbonylation catalyst, carbon monoxide, or both, as well as carbonylation reaction solvent, and may be directed to a further processing unit to remove carbonylation reaction solvent.

Figure 3:
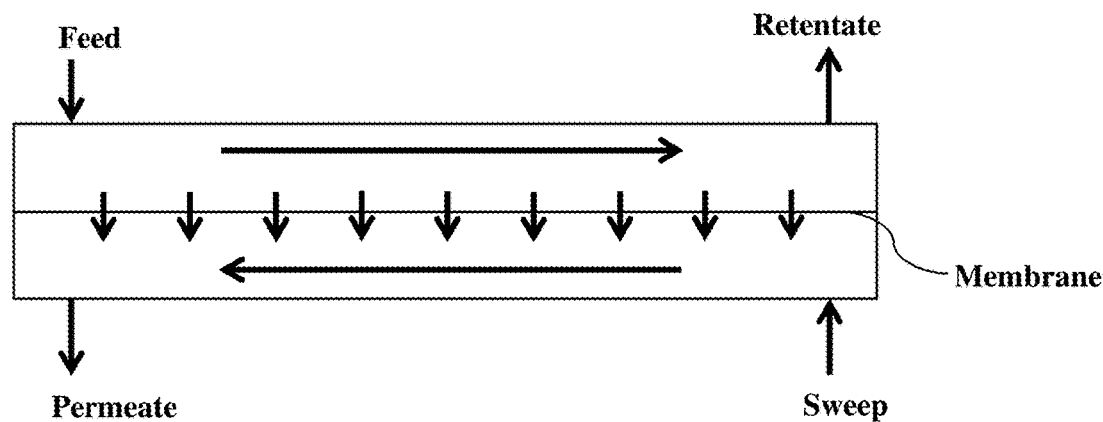

With reference to FIG. 3, yet another exemplary a membrane separation system is depicted, showing variations in the relative position of how the feed and sweep streams come in contact with the membrane, and how the permeate and retentate streams are output from the membrane.

In some embodiments, the sweep stream is a counter-current stream. A counter-current stream (i) enters the membrane separation system at the same end from which the retentate stream exits; and (ii) leaves the membrane separation system from the same end at which the feed stream enters. FIGS. 1, 2 and 3 depict the use of counter-current stream in the exemplary systems. However, it should be understood that, in other embodiments, the sweep stream may be a co-current stream. A co-current stream (i) enters the membrane separation system at the same end at which the feed stream enters; and (ii) leaves the membrane separation system from the same end at which the retentate stream leaves.

In some variations, counter-current and co-current refer to how the streams exchange mass. In one variation, in a counter-current system, the permeate stream enters with lower beta-lactone concentration (or no beta-lactone) near where the feed/retentate stream leaves with lower beta-lactone concentration. In another embodiment, in a co-current system, the permeate stream enters with lower beta-lactone concentration (or no beta-lactone) near where the feed/retentate stream leaves with higher beta-lactone concentration. In some variations of the foregoing, the counter-current system is more efficient at exchanging mass than the co-current system.

The sweep stream is saturated with one or more components from the feed stream in order to control flux across the membrane. In some embodiments, the sweep stream comprises solvent saturated with such one or more components.

Figure 8:
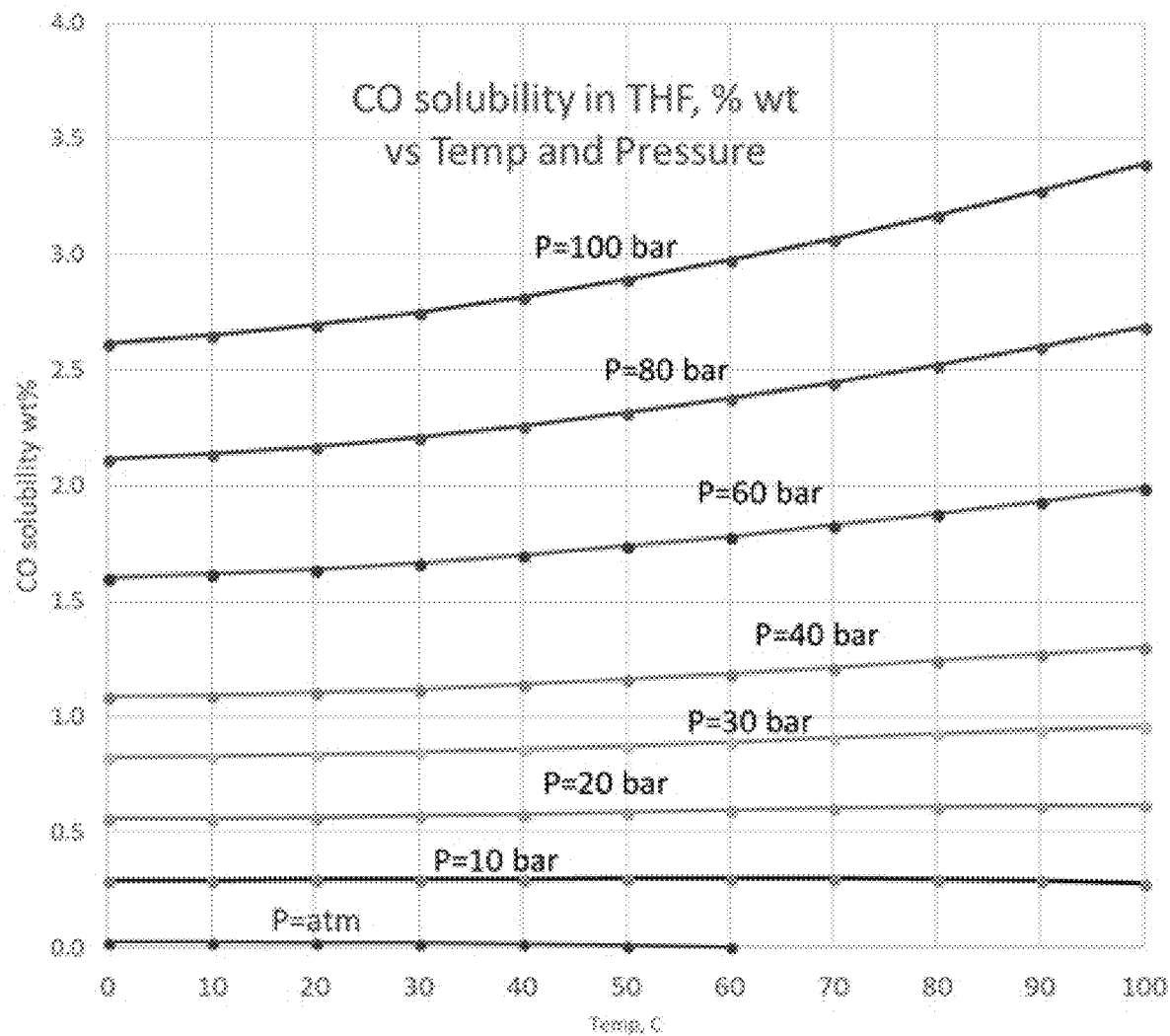
FIG. 8 depicts the variation in solubility of carbon monoxide in tetrahydrofuran (THF) as a function of temperature and pressure.

When the membrane separation system is used to separate carbonylation catalyst from beta-lactone while minimizing the flux of carbon monoxide across the membrane, in one embodiment, the sweep stream comprises solvent saturated with carbon monoxide. The solvent is saturated when the maximum possible volume of carbon monoxide that can be dissolved in a given volume of solvent at a particular temperature and pressure has been reached. FIG. 8 shows how the solubility of carbon monoxide in tetrahydrofuran varies as a function of temperature at a number of different pressures. In general, with reference to FIG. 8, the solubility of carbon monoxide in tetrahydrofuran increases at higher temperatures and higher pressures, meaning that more carbon monoxide can be dissolved in the solvent before it becomes saturated.

In certain variations, the sweep stream has a carbon monoxide content of up to about 3.5% by weight, when the process is operated at a pressure of up to 100 bar, and a constant average temperature.

Any suitable membranes may be used in the systems and methods described here to separate carbonylation catalyst from a beta-lactone product stream. See e.g., WO 2015/085295.

In some variations, the membrane comprises polyester, polyether, or mixed polyether/polyester chains growing on or within the membrane. In other variations, the membrane comprises a polymer and one or more co-polymers.

In certain embodiments, the membrane is a polyamide-based membrane. In other embodiments, the membrane is a polysiloxane-based membrane. In still other embodiments, the membrane is a polyimide-based membrane. In other variations, the membrane comprises cellulose acetate, cellulose triacetate, cellulose nitrate, regenerated cellulose, polyether ether ketones, aromatic polyamides, polyamidimides, polybenzimidazoles, polybenzimidazolones, polyacrylonitrile, polyaryl ether sulfones, polyesters, polycarbonates, polytetrafluoroethylene, polyvinylidene fluoride, polyether imide, polypropylene, polydimethylsiloxane (PDMS), polyether ether ketone (PEEK), acrylonitrile/glycidyl methacrylate (PANGMA), silane-hydrophobicized ceramic membranes, and polymers having intrinsic microporosity (PIM). In certain variations, the membrane comprises polydimethylsiloxane (PDMS), polyimide (PI), polyamidimide (PAI), acrylonitrile/glycidyl methacrylate (PANGMA), polyamide (PA), polyether ether ketone (PEEK), or polymers with intrinsic microporosity (PIM). In some variations, the membranes can have support or carrier materials onto which the separation-active layer is applied (see details regarding plate-and-frame systems below). In the case of such composite membranes, a support material is present in addition to the actual membrane. Furthermore, reinforcing materials, such as particles of inorganic oxides or inorganic fibers (e.g., ceramic or glass fibers, which increase the stability of the membranes, in particular to pressure fluctuations or high pressure differences), can be present in the membrane separation system. The membrane separation system may operate at a constant average temperature.

Several membrane configurations may be in the systems described herein. For example, a plate-and-frame membrane, a hollow fiber membrane, a spiral wound membrane, or a combination thereof may be used.

Figure 4:
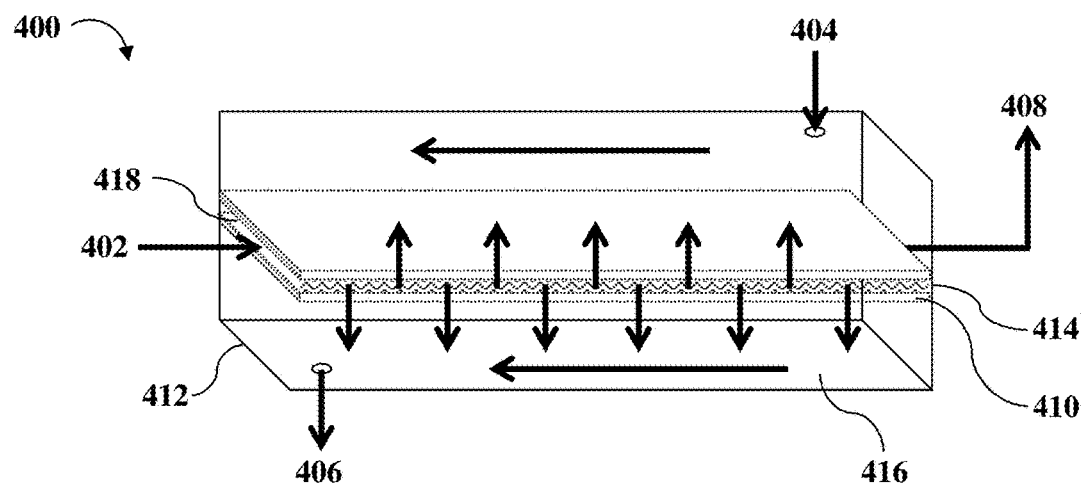
FIG. 4 depicts an exemplary plate-and-frame membrane separation system.

In one embodiment, a plate-and-frame membrane is used in the separation systems described herein. With reference to FIG. 4, system 400 is an exemplary plate-and-frame membrane system. Support screens 414 separate several sheets of membrane 410, which are all positioned within membrane holder 412. Feed stream 402 comes in contact with sheets of membrane 410 on retentate side 418, and circulates along the surface of sheets of membrane 410. Sweep stream 404 enters system 400 on the permeate side of the membrane. Permeate stream 406 forms when at least a portion of feed stream 402 crosses the sheets of membrane 410, and joins with sweep stream 404. Retentate stream 408 forms from remaining feed stream 402 after at least a portion of feed stream 402 crosses the sheets of membrane 410. Permeate stream 406 exits on permeate side 416, and retentate stream 408 exits on retentate side 418.

Figure 5:
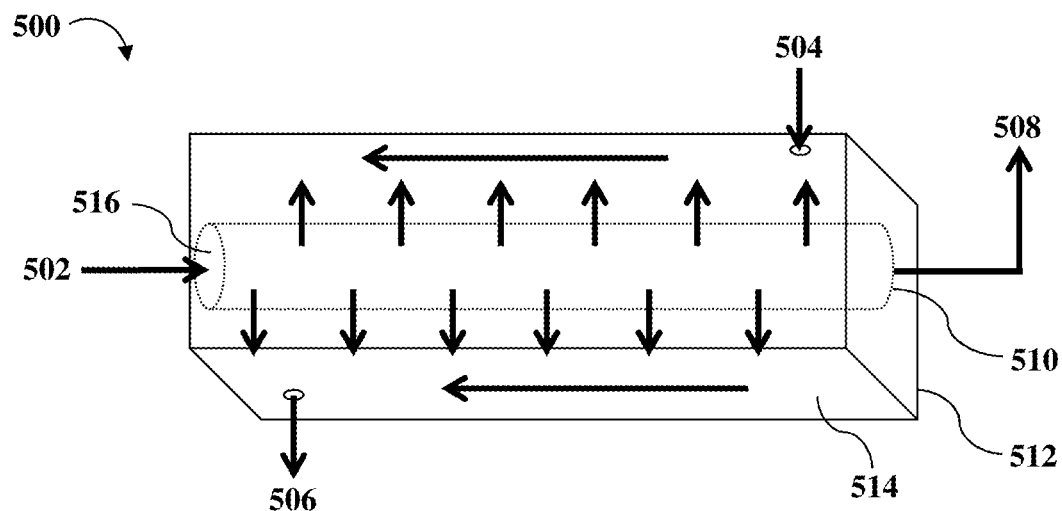
FIG. 5 depicts an exemplary hollow fiber membrane separation system.

In another embodiment, a hollow fiber membrane is used in the separation systems described herein. With reference to FIG. 5, system 500 is an exemplary hollow fiber membrane separation system. Membrane 510 takes the form of a hollow fiber or tube that is held in place by membrane holder 512. Membrane 510 has permeate side 514 and retentate side 516. Feed stream 502 enters membrane 510 on retentate side 516, and circulates along the surface of membrane 510. Sweep stream 504 enters system 500 on the permeate side of the membrane. Permeate stream 506 forms when at least a portion of feed stream 502 crosses membrane 510 to the outside of the fiber, and joins with sweep stream 504. Retentate stream 508 forms from remaining feed stream 502 after at least a portion of feed stream 502 crosses membrane 510. Permeate stream 506 exits on permeate side 514, and retentate stream 508 exits on retentate side 516.

Like system 100 in FIG. 1, systems 400 and 500 may be used, in certain variations, to separate components from a carbonylation product stream. For example, systems 400 and 500 may be configured to separate carbonylation catalyst from beta-lactone by pressure/concentration driven diffusion, while minimizing the flux of carbon monoxide across the membrane.

As depicted in FIGS. 4 and 5, sweep streams 404 and 504, respectively, are counter-current streams. It should be understood, however, that, in other embodiments of systems 400 and 500, sweep streams 404 and 504, respectively, may be co-current streams.

The flow path length, channel height/lumen diameter, and membrane pore size may impact the performance of the membrane. For example, in some variations, as flow path length increases, the transfer of molecule across the membrane can increase. In other variations, smaller channel height/lumen diameters may reduce the diffusion path, and enhance transfer of molecules across the membrane. However, the pressure drop across the device (feed inlet to retentate outlet/sweep inlet to permeate outlet) may increase. Note that such pressure drop is not the same as the trans-membrane pressure. In yet other variations, as membrane pore size increases, more material may cross the membrane at a given pressure. In one variation, the membrane selected for use in the systems herein has pores large enough to reject the larger molecules (such as carbonylation catalyst) at high efficiency, but to allow the desired products (such as beta-lactone) to easily pass.

The membrane separation systems described herein may be used to separate one or more components in a product stream, such as a carbonylation product stream produced from carbonylation of epoxides. Such carbonylation product stream becomes the feed stream for the membrane separation systems described herein, and may include, for example, beta-lactone, epoxide, carbon monoxide, carbonylation catalyst, and carbonylation reaction solvent.

Figure 6:
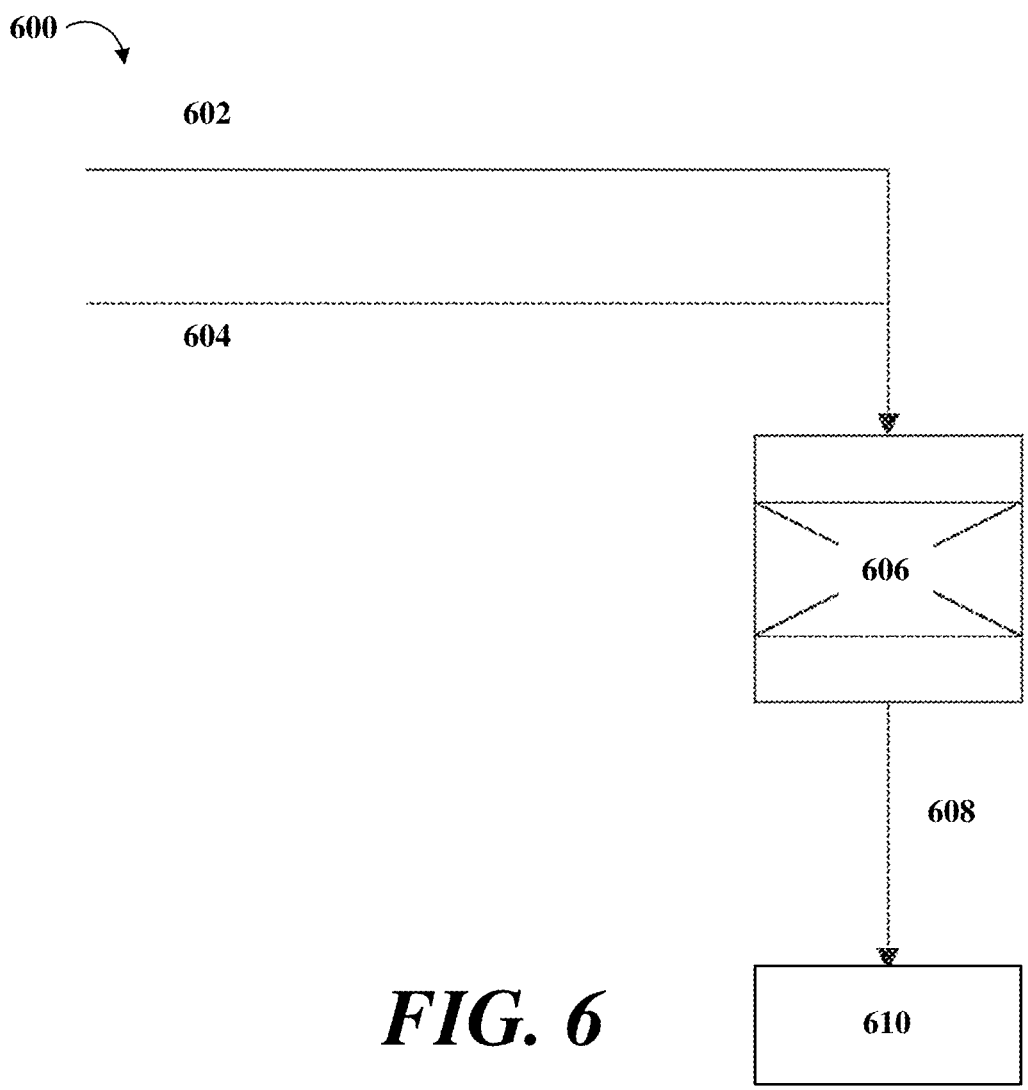
FIG. 6 depicts an exemplary beta-lactone production system that includes the use of a membrane separation system.

With reference to FIG. 6, system 600 depicts an exemplary beta-lactone production system, which includes a carbonylation system connected to a membrane separation system as described herein. The carbonylation system includes an epoxide source that outputs epoxide stream 602, as well as a carbon monoxide source that outputs carbon monoxide stream 604. The epoxide and carbon monoxide are directed into carbonylation reaction vessel 606. The epoxide undergoes carbonylation in the presence of carbonylation catalyst and reaction solvent in carbonylation reaction vessel 606 to produce carbonylation product stream 608, comprising beta-lactone, epoxide, carbon monoxide, carbonylation catalyst, and reaction solvent. Carbonylation product stream 608 is then directed to come into contact with membrane separation system 610, which separates beta-lactone from carbonylation catalyst, while minimizing the flux of carbon monoxide across the membrane.

It should be understood that one or more components may be omitted or added to system 600. In some variations, where the carbonylation catalyst is a homogenous catalyst, the carbonylation system may further include a carbonylation catalyst source that feeds carbonylation catalyst into reaction vessel 606. In other variations, the carbonylation catalyst is heterogeneous, and may be provided as a fixed bed inside reaction vessel 606. In yet other variations, the carbonylation system may further include a solvent source that feeds carbonylation reaction solvent into reaction vessel 606.

The membrane separation systems described herein receive a feed stream that includes beta-lactone, and output a permeate stream that also contains beta-lactone. The beta-lactone may be obtained from carbonylation of epoxides. Any suitable epoxides may be used. For example, as shown in Table A, the beta-lactones in Column B may be produced from the corresponding epoxide from Column A of the table.

TABLE A

| Column A | Column B |
|---|---|
| ethylene oxide | β-propiolactone |
| propylene oxide | β-butyrolactone or/and β-butyrolactone isomer |
| epichlorohydrin | chloromethyl β-lactone |
| trifluoromethyl epoxide | CF₃ β-lactone |
| glycidyl methanesulfonate | methanesulfonate β-lactone |
| glycidyl OTBS ether | OTBS β-lactone |

TABLE A-continued
| Column A | Column B |
|---|---|
| 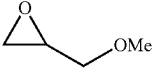 | 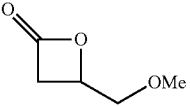 |
| 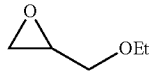 | 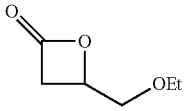 |
| 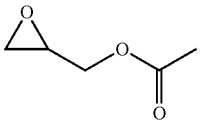 | 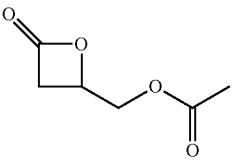 |
| 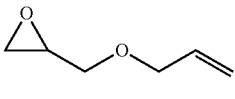 | 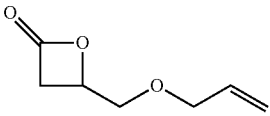 |
| 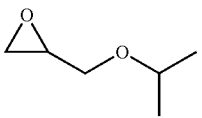 | 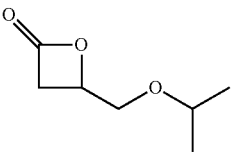 |
| 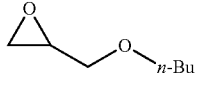 | 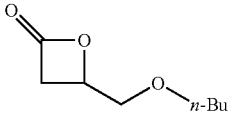 |
| 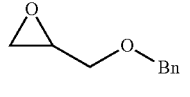 | 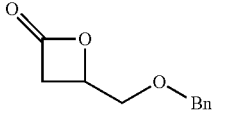 [SMILES: O=C1CC(COCc2ccccc2)O1] |
| 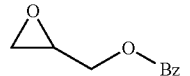 | 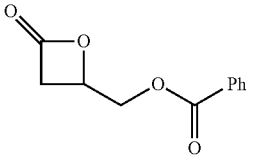 [SMILES: O=C1CC(COC(=O)c2ccccc2)O1] |
| 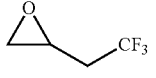 | 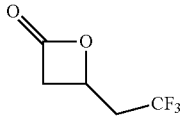 |
| 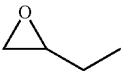 | 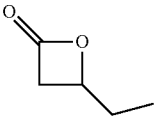 |
| 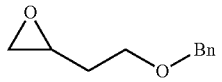 | 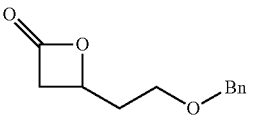 |

TABLE A-continued
| Column A | Column B |
|---|---|
| 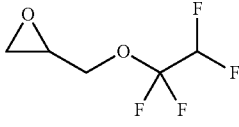 [SMILES: FC(F)C(F)(F)OCC1CO1] | 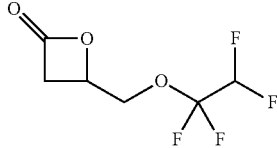 [SMILES: O=C1CC(COC(F)(F)C(F)F)O1] |
| 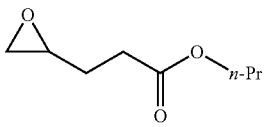 | 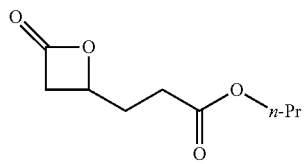 |
| 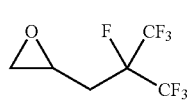 | 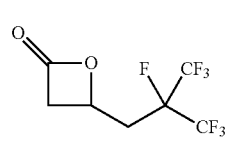 |
| 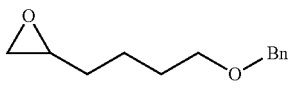 | 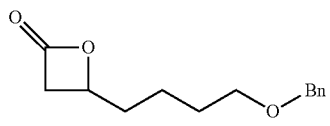 [SMILES: O=C1CC(CCCCOCc2ccccc2)O1] |
| 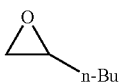 | 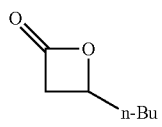 |
| 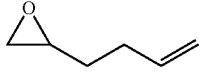 | 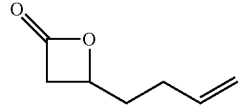 |
| 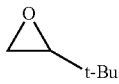 | 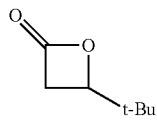 |
| 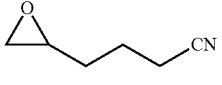 | 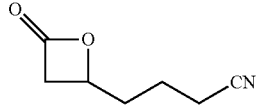 |
| 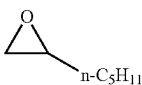 | 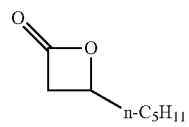 |
| 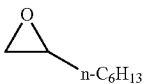 | 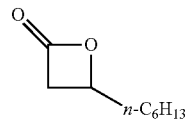 |
| 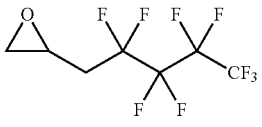 [SMILES: FC(F)(F)C(F)(F)C(F)(F)C(F)(F)CC1CO1] | 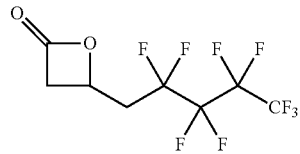 [SMILES: O=C1CC(CC(F)(F)C(F)(F)C(F)(F)C(F)(F)F)O1] |

TABLE A-continued

| Column A | Column B |
|---|---|
| (glycidyl butyrate) | (β-lactone analog) |
| (glycidyl methacrylate) | (β-lactone analog) |
| (1,2-epoxy-6-heptene) | (β-lactone analog) |
| (cyclohexyl ethylene oxide) | (β-lactone analog) |
| (styrene oxide, Ph) | (β-lactone analog, Ph) |
| (glycidyl furfuryl ether) | (β-lactone analog) |
| (glycidyl ester, n-Pr) | (β-lactone analog, n-Pr) |
| (epoxy alcohol, n-C$_5$H$_{11}$) | (β-lactone analog, n-C$_5$H$_{11}$) |
| (cyclohexylidene epoxide) | (β-lactone analog) |
| (benzyl oxirane, Ph) | (β-lactone analog, Ph) |

TABLE A-continued
| Column A | Column B |
|---|---|
| 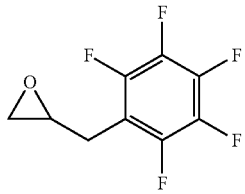 [SMILES: Fc1c(F)c(F)c(CC2CO2)c(F)c1F] | 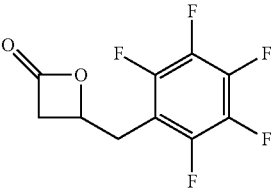 [SMILES: O=C1CC(Cc2c(F)c(F)c(F)c(F)c2F)O1] |
| 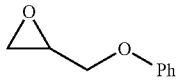 | 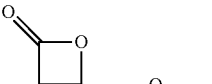 |
| 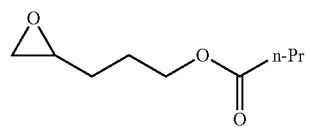 | 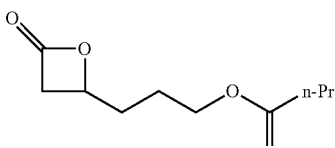 |
| 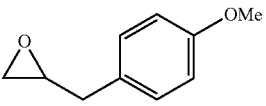 [SMILES: COc1ccc(CC2CO2)cc1] | 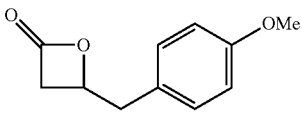 [SMILES: COc1ccc(CC2CC(=O)O2)cc1] |
| 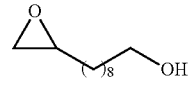 | 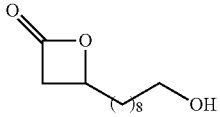 |
| 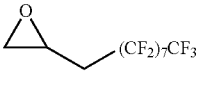 | 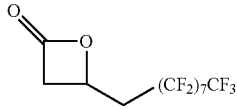 |
| 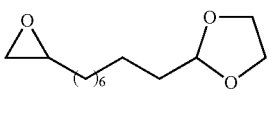 | 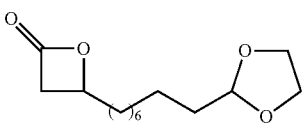 |
| 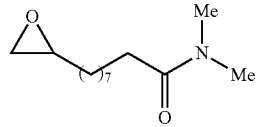 | 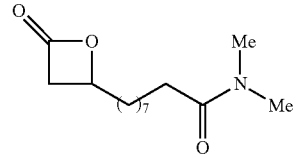 |
| 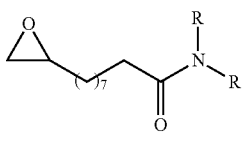 | 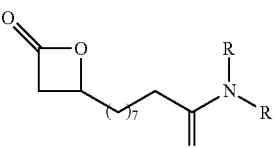 |
| 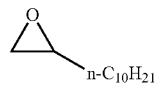 | 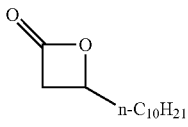 |

TABLE A-continued

| Column A | Column B |
|---|---|
| (2,2-dimethyloxirane) | (4,4-dimethyl-2-oxetanone) and/or (3,3-dimethyl-2-oxetanone) |
| (2-methyl-2-(prop-1-en-2-yl)oxirane) | (3-methyl-3-(prop-1-en-2-yl)-2-oxetanone) |
| (1-methylene-1-oxaspiro[2.5]octane) | (methylene-spiro-cyclohexyl-β-lactone) |
| ((R)-2-methyloxirane) | ((R)-4-methyl-2-oxetanone) |
| (perfluoroalkyl epoxide) | (perfluoroalkyl β-lactone) |
| ((S)-perfluoroalkyl epoxide) | ((S)-perfluoroalkyl β-lactone) |
| (amide-substituted epoxide) | (amide-substituted β-lactone) |
| ((S)-amide-substituted epoxide) | ((S)-amide-substituted β-lactone) |
| (2,3-dimethyloxirane) | (3,4-dimethyl-2-oxetanone) |

TABLE A-continued

| Column A | Column B |
|---|---|
| (structures) | (structures) |

TABLE A-continued
| Column A | Column B |
|---|---|
| 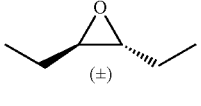 | 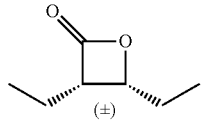 |
| 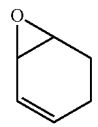 | 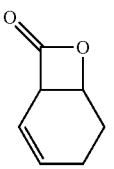 |
| 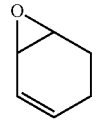 | 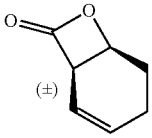 |
| 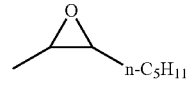 | 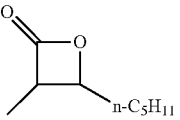 and/or 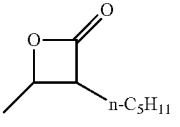 |
| 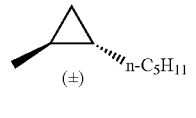 | I (±) 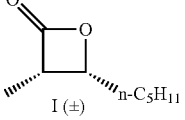 and/or II (±) 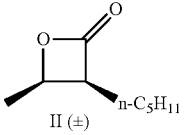 |
| 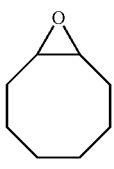 | 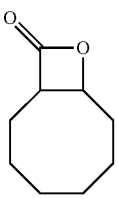 [SMILES: O=C1OC2CCCCCCC12] |
| 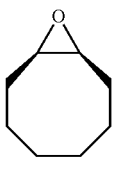 | 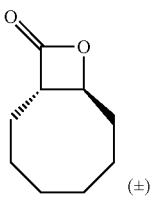 |

TABLE A-continued

| Column A | Column B |
|---|---|
| (epoxide of cyclononene) | (β-lactone fused cyclononene) |
| (epoxide of cyclononene, racemic) | (β-lactone fused cyclononene) (±) |
| Ph—epoxide—CH=CH—CH₂—OMOM | Ph—β-lactone—CH=CH—CH₂—OMOM |
| Ph—epoxide—CH=CH—CH₂—OMOM (±) | Ph—β-lactone—CH=CH—CH₂—OMOM (±) |
| Ph—epoxide—C(CH₃)=CH—CH₂—OMOM | Ph—β-lactone—C(CH₃)=CH—CH₂—OMOM |
| Ph—epoxide—C(CH₃)=CH—CH₂—OMOM (±) | Ph—β-lactone—C(CH₃)=CH—CH₂—OMOM (±) |
| (epoxide of cyclotetradecane) | (β-lactone fused cyclotetradecane) |
| (epoxide of cyclotetradecane) | (β-lactone fused cyclotetradecane) (±) |

TABLE A-continued
| Column A | Column B |
|---|---|
| 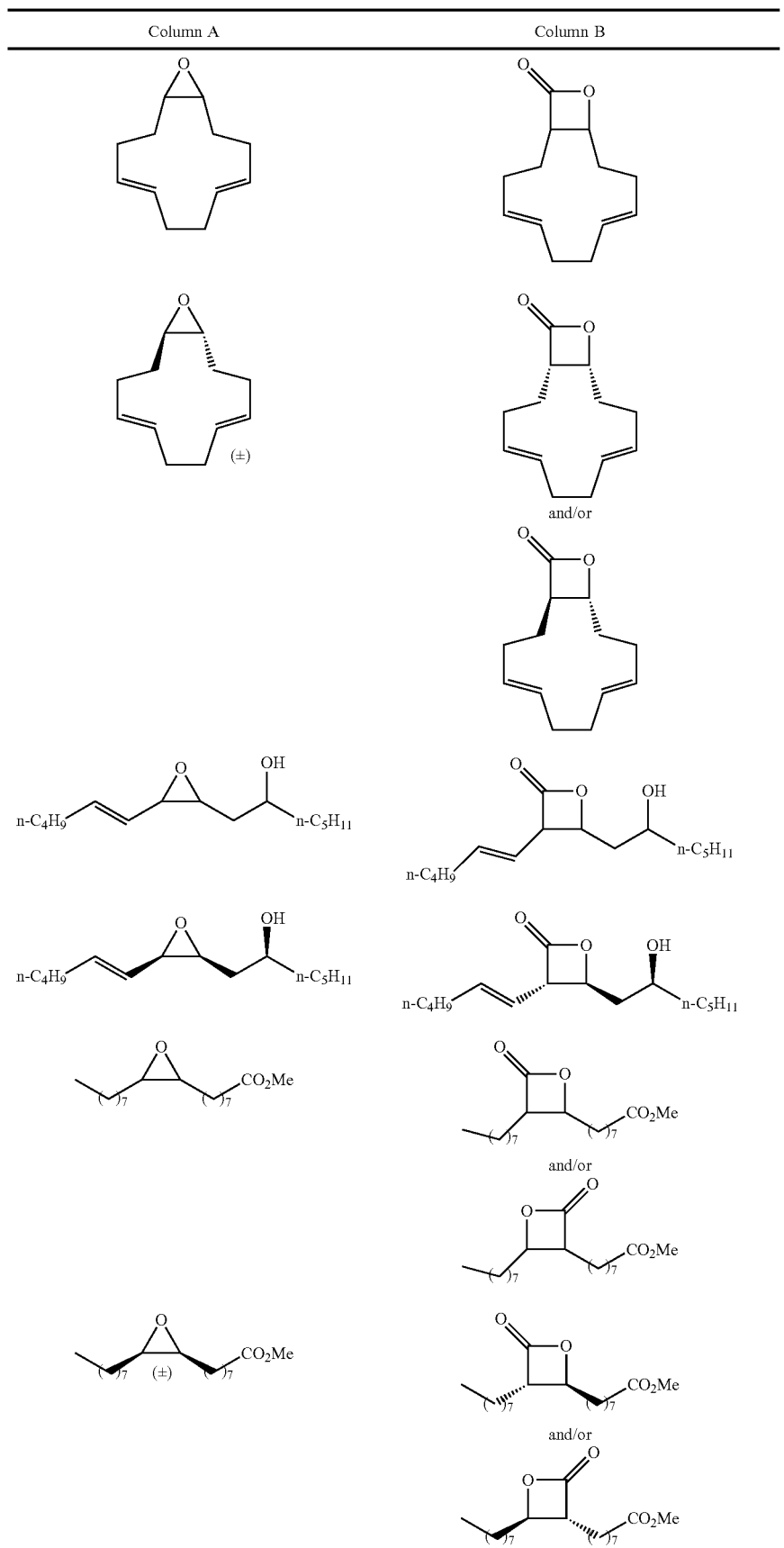 | |

TABLE A-continued

| Column A | Column B |
|---|---|

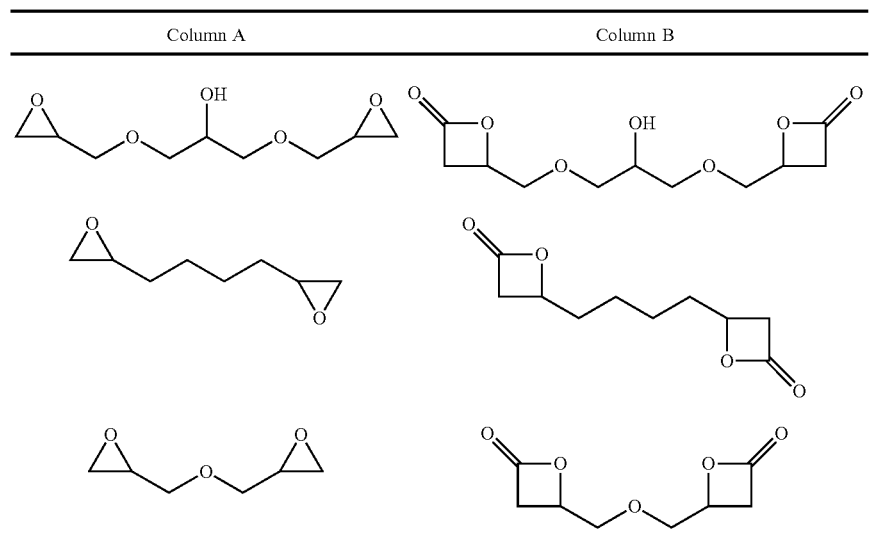

In some variations of the foregoing, the membrane separation systems described herein receive a feed stream that have a biobased content of greater than 0%, and less than 100%. In certain variations of the foregoing, the compounds present in the feed stream have a biobased content of 10% or more, 20% or more, 30% or more, 40% or more, 50% or more, 60% or more, 70% or more, 80% or more, 90% or more, 95% or more, or 99% or more.

In some variations, biobased content can be determined based on the following: % Biobased content=[Bio (Organic) Carbon]/[Total (Organic) Carbon]100%, as determined by ASTM D6866 (Standard Test Methods for Determining the Biobased Content of Solid, Liquid, and Gaseous Samples Using Radiocarbon Analysis).

In certain embodiments, the biobased content of the beta-lactone in the feed stream may depend on, for example, the biobased content of the epoxide and carbon monoxide used to make the beta-lactone in a carbonylation reaction vessel. In some variations, both the epoxide and carbon monoxide are derived from renewable sources.

The membrane separation systems described herein are contacted with a feed stream that includes solvent. In some embodiments, the solvent is the reaction solvent from the carbonylation reaction that provides the feed stream for the membrane separation systems. In some variations, the permeate stream, the counter-current stream, and/or the retentate stream also include(s) the solvent.

In certain variations, the feed stream comprises a single solvent. In other variations, the feed stream comprises a mixture of solvents. Suitable solvents are ethers, hydrocarbons, and non-protic polar solvents, including, for example, tetrahydrofuran, sulfolane, N-methyl pyrrolidone, 1,3 dimethyl-2-imidazolidinone, diglyme, triglyme, tetraglyme, diethylene glycol dibutyl ether, isosorbide ethers, methyl tertbutyl ether, diethylether, diphenyl ether, 1,4-dioxane, ethylene carbonate, propylene carbonate, butylene carbonate, dibasic esters, diethyl ether, acetonitrile, ethyl acetate, dimethoxy ethane, acetone, and methylethyl ketone. In one variation, the solvent comprises tetrahydrofuran. In another variation, beta-lactone may be used as a co-solvent.

The membrane separation systems described herein are contacted with a feed stream that includes catalyst. In some embodiments, the catalyst is carbonylation catalyst from the carbonylation reaction.

In certain variations, the catalyst comprises a metal carbonyl compound. In one variation, a single metal carbonyl compound is present in the feed stream. In another variation, mixtures of two or more metal carbonyl compounds are present. Thus, when a metal carbonyl compound "comprises", e.g., a neutral metal carbonyl compound, it is understood that the metal carbonyl compound present can be a single neutral metal carbonyl compound, or a neutral metal carbonyl compound in combination with one or more metal carbonyl compounds.

In some embodiments, the metal carbonyl comprises an anionic metal carbonyl moiety. In other embodiments, the metal carbonyl compound comprises a neutral metal carbonyl compound. In some embodiments, the metal carbonyl compound comprises a metal carbonyl hydride or a hydrido metal carbonyl compound. In certain embodiments, the hydrido metal carbonyl comprises one or more of HCo(CO)4, HCoQ(CO)3, HMn(CO)5, HMn(CO)4Q, HW(CO)3Q, HRe(CO)5, HMo(CO)3Q, HOs(CO)2Q, HMo(CO)2Q2, HFe(CO2)Q, HW(CO)2Q2, HRuCOQ2, H2Fe(CO)4 or H2Ru(CO)4, where each Q is independently as defined above and in the classes and subclasses herein. In certain embodiments, the metal carbonyl hydride comprises HCo(CO)4; HCo(CO)3PR3, where each R is independently an optionally substituted aryl group, an optionally substituted C1-20 aliphatic group, an optionally substituted C1-10 alkoxy group, or an optionally substituted phenoxy group; HCo(CO)3cp, where cp represents an optionally substituted pentadienyl ligand; HMn(CO)5; or H2Fe(CO)4.

In some embodiments, the metal carbonyl compound comprises an anionic metal carbonyl species. In some embodiments, such anionic metal carbonyl species have the general formula [QdM'e(CO)w]y-, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In some embodiments, the anionic metal carbonyl has the general formula [QM' (CO)w]y-, where Q is any ligand and need not be present, M' is a metal atom, w is a number such as to provide the stable anionic metal carbonyl, and y is the charge of the anionic metal carbonyl.

In some embodiments, the anionic metal carbonyl species includes monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, for example, [Co(CO)4]-, [Ti(CO)6]2-, [V(CO)6]-, [Rh(CO)4]-, [Fe(CO)4]2-, [Ru(CO)4]2-, [Os(CO)4]2-, [Cr2(CO)10]2-, [Fe2(CO)8]2-, [Tc(CO)5]-, [Re(CO)5]-, and [Mn(CO)5]-. In some embodiments, the anionic metal carbonyl comprises [Co(CO)4]-. In some embodiments, a mixture of two or more anionic metal carbonyl complexes may be present in the carbonylation catalysts used in the methods.

In embodiments where the metal carbonyl compound is an anionic species, one or more cations must also necessarily be present. In some embodiments, the cation associated with an anionic metal carbonyl compound comprises a reaction component of another category described herein. For example, in some embodiments, the metal carbonyl anion is associated with a cationic Lewis acid. In other embodiments a cation associated with an anionic metal carbonyl compound is a simple metal cation such as those from Groups 1 or 2 of the periodic table (e.g., Na+, Li+, K+, and Mg2+). In other embodiments, a cation associated with the anionic metal carbonyl compound is a bulky non electrophilic cation such as an 'onium salt' (e.g., Bu4N+, PPN+, Ph4P+, and Ph4As+). In other embodiments, the metal carbonyl anion is associated with a protonated nitrogen compound (e.g., a cation may comprise a compound such as MeTBD-H+, DMAP-H+, DABCO-H+, and DBU-H+).

In some embodiments, the catalyst comprises a neutral metal carbonyl compound. In some embodiments, such neutral metal carbonyl compound has the general formula QdM'e(CO)w', where Q is any ligand and need not be present, M' is a metal atom, d is an integer between 0 and 8 inclusive, e is an integer between 1 and 6 inclusive, and w' is a number such as to provide the stable neutral metal carbonyl complex. In some embodiments, the neutral metal carbonyl has the general formula QM'(CO)w'. In some embodiments, the neutral metal carbonyl has the general formula M'(CO)w'. In some embodiments, the neutral metal carbonyl has the general formula QM'2(CO)w'. In some embodiments, the neutral metal carbonyl has the general formula M'2(CO)w'. The metal carbonyl compounds may include, for example, Ti(CO)7, V2(CO)12, Cr(CO)6, Mo(CO)6, W(CO)6, Mn2(CO)10, Tc2(CO)10, Re2(CO)10, Fe(CO)5, Ru(CO)5, Os(CO)5, Ru3(CO)12, Os3(CO)12 Fe3(CO)12, Fe2(CO)9, Co4(CO)12, Rh4(CO)12, Rh6(CO)16, Ir4(CO)12, Co2(CO)8, and Ni(CO)4.

In some embodiments, the metal carbonyl compound has no ligands Q. In other embodiments, one or more ligands Q are present on the metal carbonyl compound. In some embodiments, where Q is present, each occurrence of Q is selected from the group consisting of phosphine ligands, amine ligands, cyclopentadienyl ligands, heterocyclic ligands, nitriles, phenols, and combinations of two or more of these. In some embodiments, one or more of the CO ligands of any of the metal carbonyl compounds and described above is replaced with a ligand Q. In some embodiments, Q is a phosphine ligand, a triaryl phosphine ligand, trialkyl phosphine ligand, a phosphite ligand, an optionally substituted cyclopentadienyl ligand, cp, cp*, an amine, or a heterocycle.

In some embodiments, the carbonylation catalyst further includes a Lewis acidic component. In some embodiments, the carbonylation catalyst includes an anionic metal carbonyl complex and a cationic Lewis acidic component. In some embodiments, the metal carbonyl complex includes a carbonyl cobaltate and the Lewis acidic co-catalyst includes a metal-centered cationic Lewis acid. In some embodiments, an included Lewis acid comprises a boron compound.

In certain embodiments, for any of the metal carbonyl compounds described above, M' comprises a transition metal. In certain embodiments, for any of the metal carbonyl compounds described above, M' is selected from Groups 5 (Ti) to 10 (Ni) of the periodic table. In certain embodiments, M' is a Group 9 metal. In certain embodiments, M' is Co. In certain embodiments, M' is Rh. In certain embodiments, M' is Ir. In certain embodiments, M' is Fe. In certain embodiments, M' is Mn.

In some embodiments, wherein the Lewis acid in the carbonylation catalyst comprises a boron compound, the boron compound comprises a trialkyl boron compound or a triaryl boron compound. In some embodiments, an included boron compound comprises one or more boron-halogen bonds. In some embodiments, where an included boron compound comprises one or more boron-halogen bonds, the compound is a dialkyl halo boron compound (e.g., R2BX), a dihalo monoalkyl compound (e.g., RBX2), an aryl halo boron compound (e.g., Ar2BX or ArBX2), or a trihalo boron compound (e.g., BCl3 or BBr3), wherein each R is an alkyl group; each X is a halogen; and each Ar is an aromatic group.

In some embodiments, where the included Lewis acid comprises a metal-centered cationic Lewis acid, the Lewis acid is a cationic metal complex. In some embodiments, the cationic metal complex has its charge balanced either in part, or wholly by one or more anionic metal carbonyl moieties. Suitable anionic metal carbonyl compounds include those described above. In some embodiments, there are 1 to 17 such anionic metal carbonyls balancing the charge of the metal complex. In some embodiments, there are 1 to 9 such anionic metal carbonyls balancing the charge of the metal complex. In some embodiments, there are 1 to 5 such anionic metal carbonyls balancing the charge of the metal complex. In some embodiments, there are 1 to 3 such anionic metal carbonyls balancing the charge of the metal complex.

In some embodiments, the carbonylation catalysts includes a cationic metal complex. In certain variations, the metal complex has the formula [(Lc)vMb]z+, wherein:

Lc is a ligand where, when two or more Lc are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In some embodiments, the Lewis acids conform to structure I:

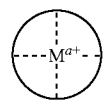

I wherein:

 is a multidentate ligand;
M is a metal atom coordinated to the multidentate ligand; and
a is the charge of the metal atom and ranges from 0 to 2.

In some embodiments, the metal complexes conform to structure II:

II wherein a is as defined above (each a may be the same or different), and
M1 is a first metal atom;
M2 is a second metal atom;

comprises a multidentate ligand system capable of coordinating both metal atoms.

For sake of clarity, and to avoid confusion between the net and total charge of the metal atoms in complexes I and II and other structures herein, the charge (a+) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net charge of +1, and a would be 1.

Suitable multidentate ligands include, for example, porphyrin derivatives 1, salen ligands 2, dibenzotetramethyl-tetraaza[14]annulene (tmtaa) ligands 3, phthalocyaninate ligands 4, the Trost ligand 5, tetraphenylporphyrin ligands 6, and corrole ligands 7. In some embodiments, the multidentate ligand is a salen ligand. In other embodiments, the multidentate ligand is a porphyrin ligand. In other embodiments, the multidentate ligand is a tetraphenylporphyrin ligand. In other embodiments, the multidentate ligand is a corrole ligand. Any of the foregoing ligands can be unsubstituted or can be substituted. Numerous variously substituted analogs of these ligands are known in the art and will be apparent to the skilled artisan.

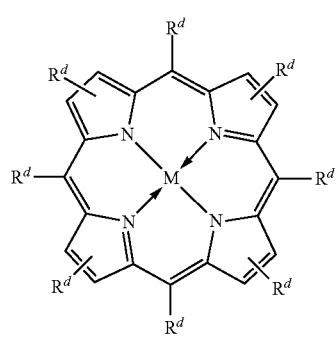

1

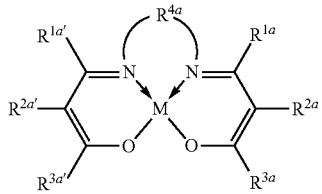

2

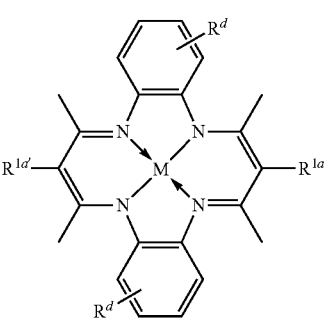

3

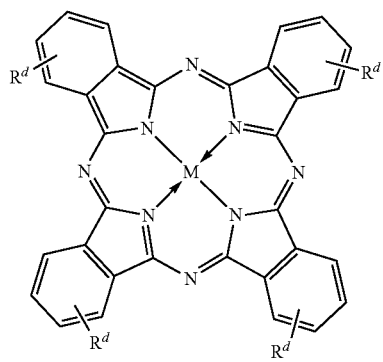

4

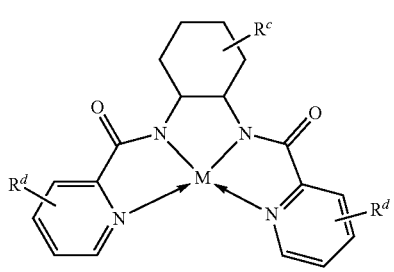

5

-continued

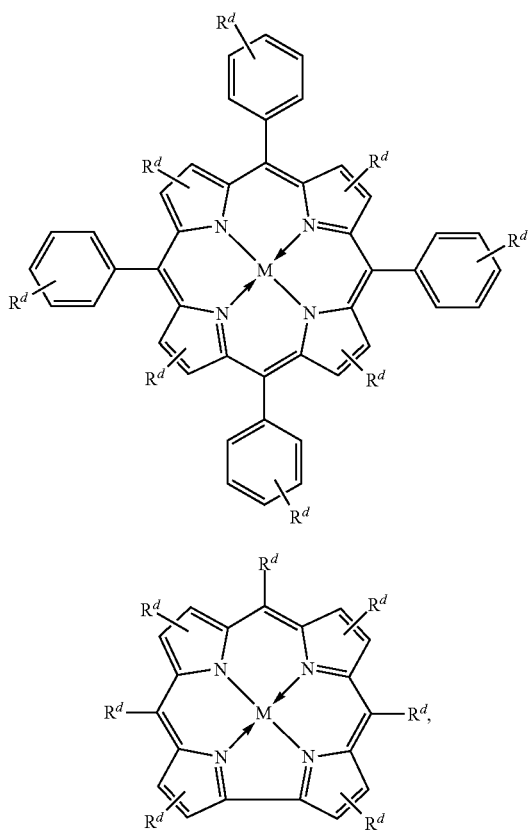

wherein each of Rc, Rd, R1a, R2a, R3a, R4a, R1a', R2a', R3a', and M, is as defined and described in the classes and subclasses herein.

In some embodiments, the carbonylation catalysts comprise metal-porphinato complexes. In some embodiments, the moiety

has the structure:

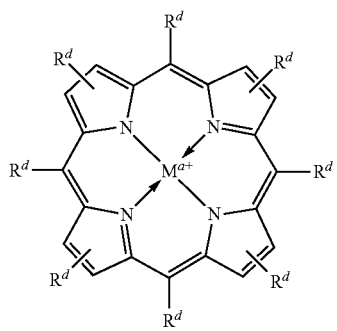

wherein:
each of M and a is as defined above and described in the classes and subclasses herein, and
Rd at each occurrence is independently hydrogen, halogen, —OR4, —NRy2, —SRy, —CN, —NO2, —SO2Ry, —SORy, —SO2NRy2; —CNO, —NRySO2Ry, —NCO, —N3, —SiRy3; or an optionally substituted group selected from the group consisting of C1-20 aliphatic; C1-20 heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more Rd groups may be taken together to form one or more optionally substituted rings;
each Ry is independently hydrogen, an optionally substituted group selected the group consisting of acyl; carbamoyl, arylalkyl; 6- to 10-membered aryl; C1-12 aliphatic; C1-12 heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two Ry on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and
each R4 is independently is a hydroxyl protecting group or Ry.

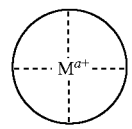

In some embodiments, the moiety has the structure:

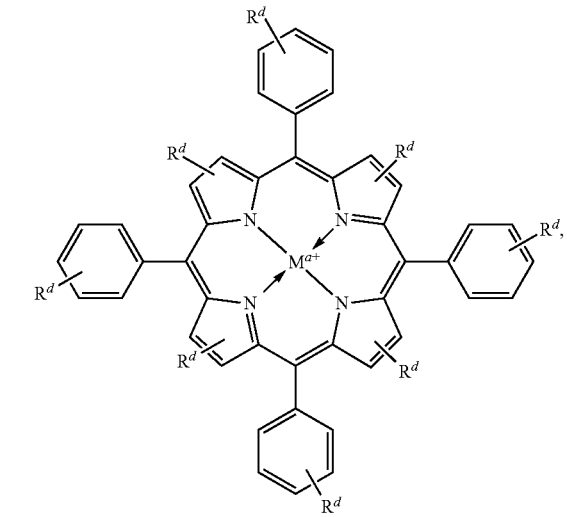

where M, a and Rd are as defined above and in the classes and subclasses herein.

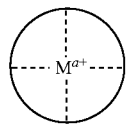

In some embodiments, the moiety has the structure:

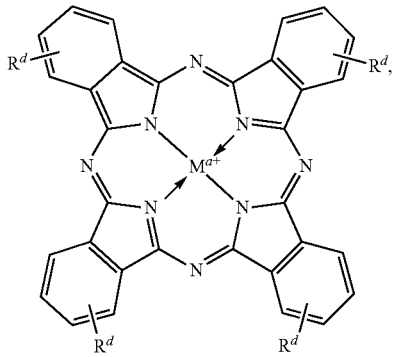

where M, a and Rd are as defined above and in the classes and subclasses herein.

In some embodiments, the carbonylation catalysts include Lewis acids comprising metallo salenate complexes. In some embodiments, the moiety

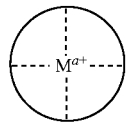

has the structure:

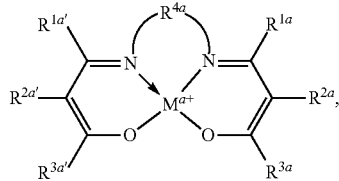

wherein:
M, and a are as defined above and in the classes and subclasses herein.
R1a, R1a', R2a, R2a', R3a, and R3a' are independently hydrogen, halogen, —OR4, —NRy2, —SRy, —CN, —NO2, —SO2Ry, —SORy, —SO2NRy2; —CNO, —NRySO2Ry, —NCO, —N3, —SiRy3; or an optionally substituted group selected from the group consisting of C1-20 aliphatic; C1-20 heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; wherein each R4, and Ry is independently as defined above and described in classes and subclasses herein, wherein any of (R2a' and R3a'), (R2a and R3a), (R1a and R2a), and (R1a' and R2a') may optionally be taken together with the carbon atoms to which they are attached to form one or more rings which may in turn be substituted with one or more Ry groups;
and
R4a is selected from the group consisting of:

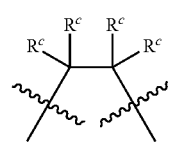 e)

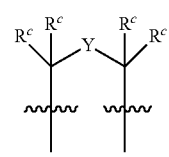 f)

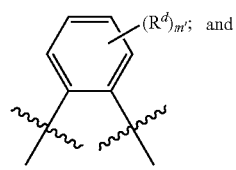 g)

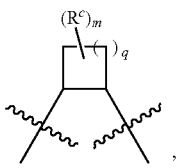 h)

where
Rc at each occurrence is independently hydrogen, halogen, —OR4, —NRy2, —SRy, —CN, —NO2, —SO2Ry, —SORy, —SO2NRy2; —CNO, —NRySO2Ry, —NCO, —N3, —SiRy3; or an optionally substituted group selected from the group consisting of C1-20 aliphatic; C1-20 heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;
where:
two or more Rc groups may be taken together with the carbon atoms to which they are attached and any intervening atoms to form one or more rings;
when two Rc groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;

where R4 and Ry are as defined above and in classes and subclasses herein;

Y is a divalent linker selected from the group consisting of: —NRy-, —N(Ry)C(O)—, —C(O)NRy-, —O—, —C(O)—, —OC(O)—, —C(O)O—, —S—, —SO—, —SO2-, —C(=S)—, —C(=NRy)-, —N=N—; a polyether; a C3 to C8 substituted or unsubstituted carbocycle; and a C1 to C8 substituted or unsubstituted heterocycle;

m' is 0 or an integer from 1 to 4, inclusive;

q is 0 or an integer from 1 to 4, inclusive; and x is 0, 1, or 2.

In some embodiments, the Lewis acid comprises a metallo salen compound, as shown in formula Ia:

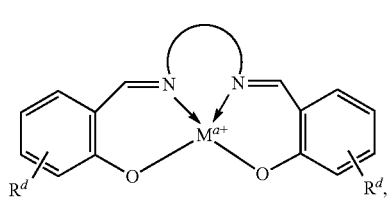

Ia wherein each of M, Rd, and a, is as defined above and in the classes and subclasses herein, ⌒ represents is an optionally substituted moiety linking the two nitrogen atoms of the diamine portion of the salen ligand, where ⌒ is selected from the group consisting of a C3-C14 carbocycle, a C6-C10 aryl group, a C3-C14 heterocycle, and a C5-C10 heteroaryl group; or an optionally substituted C2-20 aliphatic group, wherein one or more methylene units are optionally and independently replaced by —NRy-, —N(Ry)C(O)—, —C(O)N(Ry)-, —OC(O)N(Ry)-, —N(Ry)C(O)O—, —OC(O)O—, —O—, —C(O)—, —OC(O)—, —C(O)O—, —S—, —SO—, —SO2-, —C(=S)—, —C(=NRy)-, —C(=NORy)- or —N=N—.

In some embodiments of metal complexes having formula Ia above, at least one of the phenyl rings comprising the salicylaldehyde-derived portion of the metal complex is independently selected from the group consisting of:

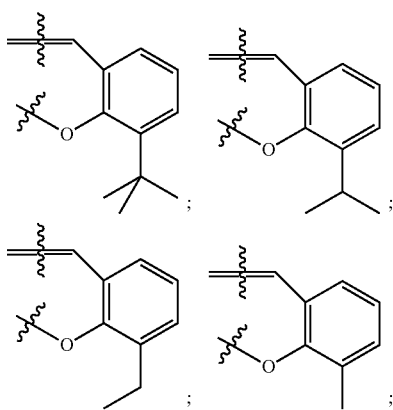

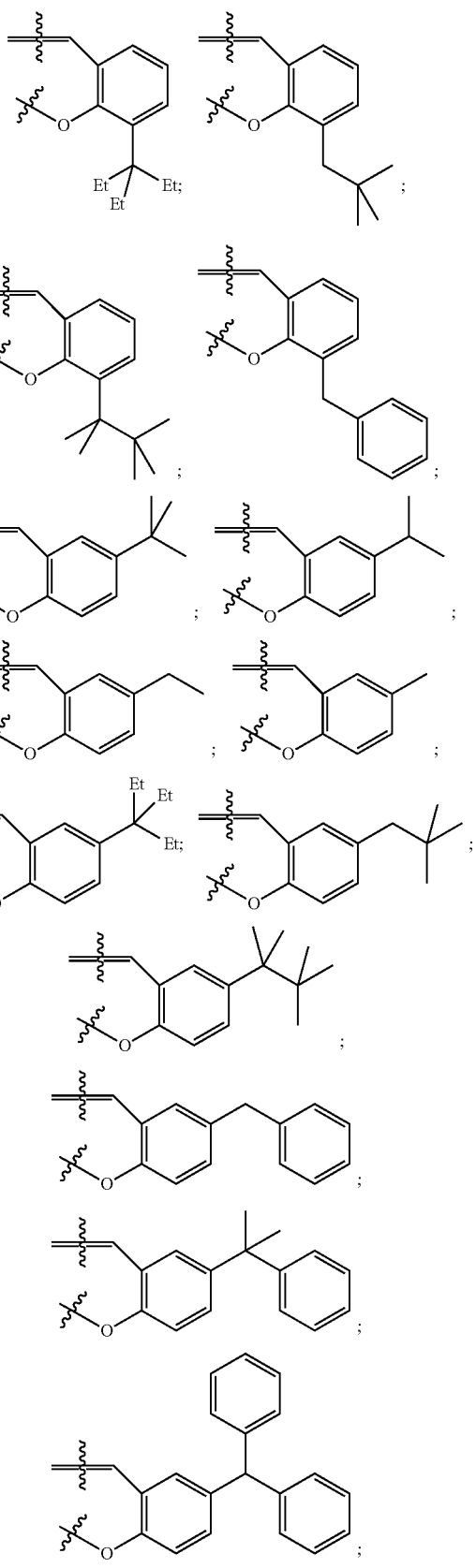

-continued

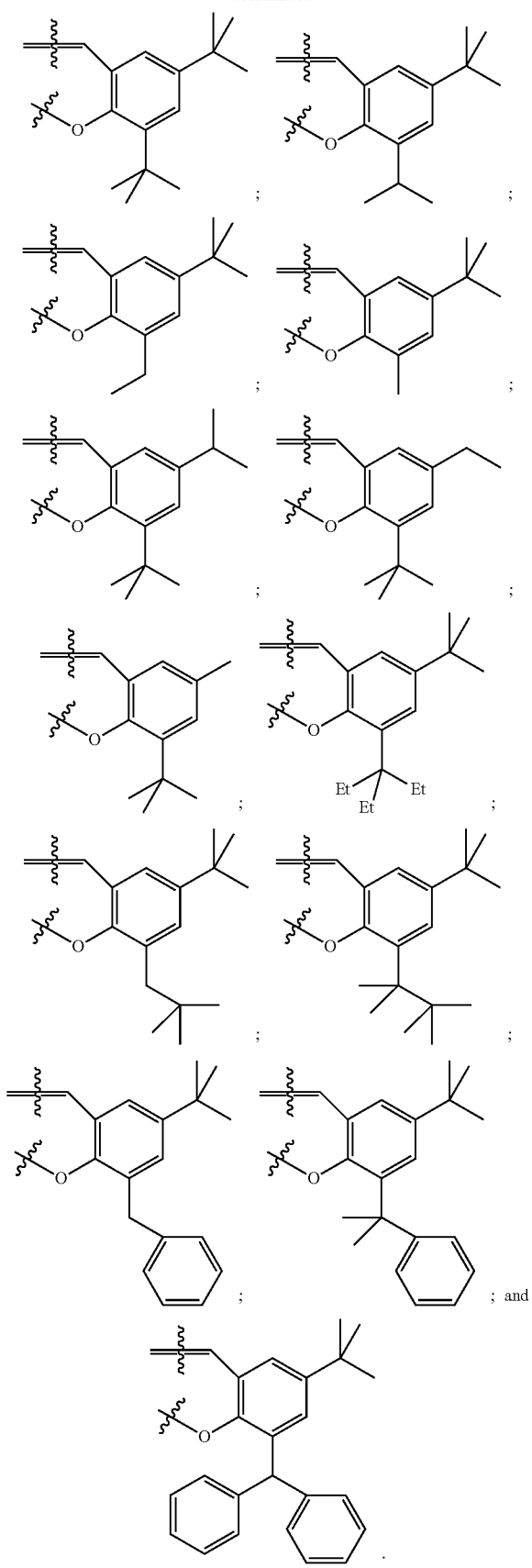

In some embodiments, the Lewis acid comprises a metallo salen compound, conforming to one of formulae Va or Vb:

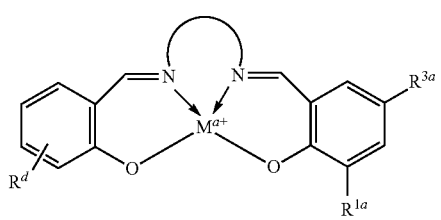

Va or

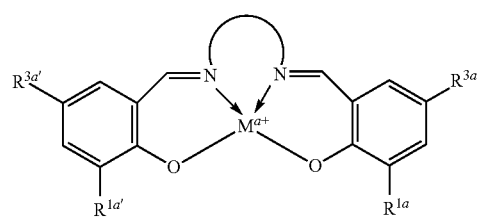

Vb where M, a, Rd, R1a, R3a, R1a', R3a', and 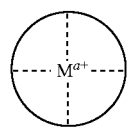, are as defined above and in the classes and subclasses herein.

In some embodiments, the metal complexes have formulae Va or Vb, where each R1a and R3a is, independently, optionally substituted C1-C20 aliphatic.

In some embodiments, the moiety ⌒ comprises an optionally substituted 1,2-phenyl moiety.

In some embodiments, Lewis acids included in carbonylation catalysts described herein comprise metal-tmtaa complexes. In some embodiments, the moiety

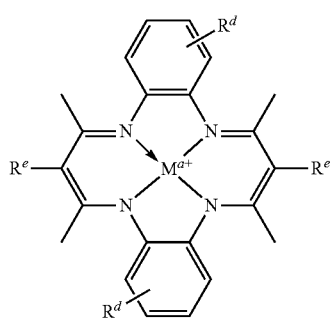

has the structure:

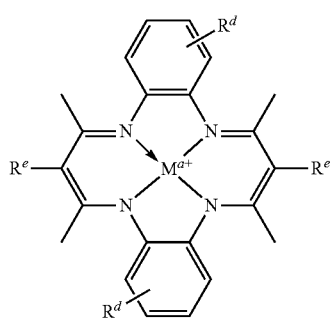

where M, a and Rd are as defined above and in the classes and subclasses herein, and Re at each occurrence is independently hydrogen, halogen, —OR, —NRy2, —SRy, —CN, —NO2, —SO2Ry, —SORy, —SO2NRy2; —CNO, —NRySO2Ry, —NCO, —N3, —SiRy3; or an optionally substituted group selected from the group consisting of C1-20 aliphatic; C1-20 heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In some embodiments, the moiety

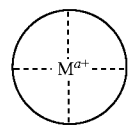

has the structure:

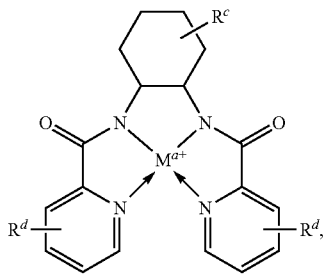

where each of M, a, Rc and Rd is as defined above and in the classes and subclasses herein.

In some embodiments, where carbonylation catalysts include a Lewis acidic metal complex, the metal atom is selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium.

In some embodiments, M has an oxidation state of +2. In some embodiments, M is Zn(II), Cu(II), Mn(II), Co(II), Ru(II), Fe(II), Co(II), Rh(II), Ni(II), Pd(II) or Mg(II). In some embodiments M is Zn(II). In some embodiments M is Cu(II).

In some embodiments, M has an oxidation state of +3. In some embodiments, M is Al(III), Cr(III), Fe(III), Co(III), Ti(III) In(III), Ga(III) or Mn(III). In some embodiments M is Al(III). In some embodiments, M is Cr(III).

In some embodiments, M has an oxidation state of +4. In some embodiments, M is Ti(IV) or Cr(IV).

In some embodiments, M1 and M2 are each independently a metal atom selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium. In some embodiments, M1 and M2 are the same. In some embodiments, M1 and M2 are the same metal, but have different oxidation states. In some embodiments, M1 and M2 are different metals.

In some embodiments, one or more of M1 and M2 has an oxidation state of +2. In some embodiments, M1 is Zn(II), Cu(II), Mn(II), Co(II), Ru(II), Fe(II), Co(II), Rh(II), Ni(II), Pd(II) or Mg(II). In some embodiments M1 is Zn(II). In some embodiments M1 is Cu(II). In some embodiments, M2 is Zn(II), Cu(II), Mn(II), Co(II), Ru(II), Fe(II), Co(II), Rh(II), Ni(II), Pd(II) or Mg(II). In some embodiments M2 is Zn(II). In some embodiments M2 is Cu(II).

In some embodiments, one or more of M1 and M2 has an oxidation state of +3. In some embodiments, M1 is Al(III), Cr(III), Fe(III), Co(III), Ti(III) In(III), Ga(III) or Mn(III). In some embodiments M1 is Al(III). In some embodiments M1 is Cr(III). In some embodiments, M2 is Al(III), Cr(III), Fe(III), Co(III), Ti(III) In(III), Ga(III) or Mn(III). In some embodiments M2 is Al(III). In some embodiments M2 is Cr(III).

In some embodiments, one or more of M1 and M2 has an oxidation state of +4. In some embodiments, M1 is Ti(IV) or Cr(IV). In some embodiments, M2 is Ti(IV) or Cr(IV).

In some embodiments, the metal-centered Lewis-acidic component of the catalyst includes a dianionic tetradentate ligand. In some embodiments, the dianionic tetradentate ligand is selected from the group consisting of: porphyrin ligands; salen ligands; dibenzotetramethyltetraaza[14]annulene (tmtaa) ligands; phthalocyaninate ligands; and the Trost ligand.

In some embodiments, the carbonylation catalyst includes a carbonyl cobaltate in combination with an aluminum porphyrin compound. In some embodiments, the carbonylation catalyst is [(TPP)Al(THF)2][Co(CO)4], where TPP stands for tetraphenylporphyrin and THF stands for tetrahydrofuran.

In some embodiments, the carbonylation catalyst includes a carbonyl cobaltate in combination with a chromium porphyrin compound.

In some embodiments, the carbonylation catalyst includes a carbonyl cobaltate in combination with a chromium salen compound. In some embodiments, the carbonylation catalyst includes a carbonyl cobaltate in combination with a chromium salophen compound.

In some embodiments, the carbonylation catalyst includes a carbonyl cobaltate in combination with an aluminum salen compound. In some embodiments, the carbonylation catalyst includes a carbonyl cobaltate in combination with an aluminum salophen compound.

In some embodiments, one or more neutral two electron donors coordinate to M M1 or M2 and fill the coordination valence of the metal atom. In some embodiments, the neutral two electron donor is a solvent molecule. In some embodiments, the neutral two electron donor is an ether. In some embodiments, the neutral two electron donor is tetrahydrofuran, diethyl ether, acetonitrile, carbon disulfide, or pyridine. In some embodiments, the neutral two electron donor is tetrahydrofuran. In some embodiments, the neutral two electron donor is an epoxide. In some embodiments, the neutral two electron donor is an ester or a lactone.

EXAMPLES

The following Example is merely illustrative and is not meant to limit any aspects of the present disclosure in any way.

Example 1

Membrane Process Flow

This examples describes a general membrane process flow to separate components in a feed stream (F) that is made up of a solvent (S, a small molecule), product (P, a small molecule), byproduct (B, a small molecule), catalyst (C, a large molecule), and a saturated, dissolved gas (G, a small molecule).

Figure 7:
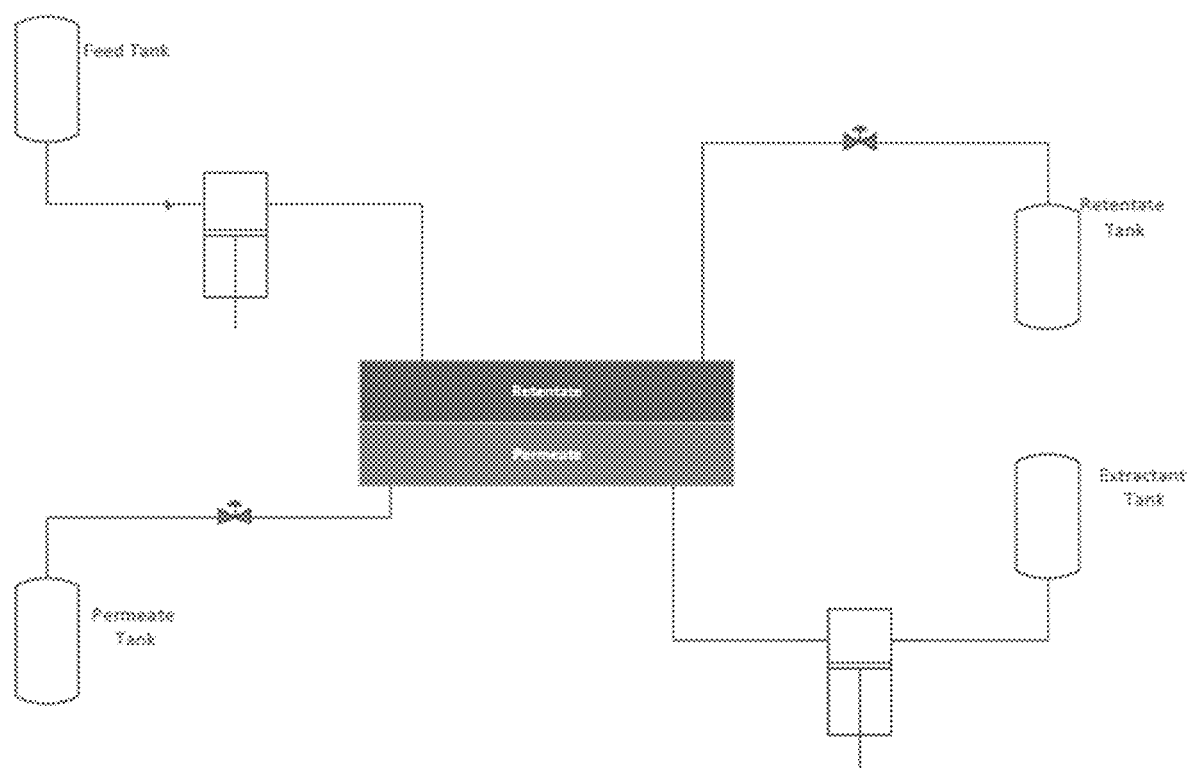
FIG. 7 depicts an exemplary membrane separation system used to separate a carbonylation catalyst from a feed stream.

Feed stream (F) is introduced under pressure (P1) to the retentate side of the membrane cell. Simultaneously, an extracting fluid (E) consisting of solvent (S) and a saturated, dissolved gas (G) is introduced either co-currently or counter-currently under pressure (P2) to the permeate side of the membrane cell. An example of the setup for this example is depicted in FIG. 7. The small molecules in this example have a formula weight of less than or equal to 150 Da, and the large molecules have a formula weight greater than 500 Da.

The membrane composition and structure are selected such that S, P, B, and G can transverse the membrane; C is unable to transverse the membrane due to its molecular size. Fluid leaving the retentate side of the cell is depleted of P and B, with substantially the same amounts of S, C, and G as in the feed fluid is returned to the reactor or retentate tank for additional processing. Fluid leaving the permeate side of the cell is enriched in P and B, with substantially the same amounts of S and G in the extracting fluid is sent to further processing or a permeate tank. Stated another way, concentrations on the permeate side and the retentate side are nearly equal for every component (S, P, B, G) except for the large molecular weight species (C) which are concentrated on the retentate side of the membrane.

In general, P1≥P2. Both P and B are transferred through the membrane due to the partial pressure gradient between the feed and extracting fluids. In this example, both P1 and P2 can range from 0-70 barg (0-1029 psig), and the absolute difference between P1 and P2 does not exceed 15 barg (220 psig), so as to avoid or minimize damage to the membrane. A small amount of S and/or G may transfer through the membrane from the retentate to the permeate side due to pressure gradient.

In this example, the flow rate of the extracting fluid (FE) rate is greater than the flow rate of feed (FF), or FE≥FF, and preferably FE/FF≥1.5.

The retentate return to the reactor may be replaced by a retentate tank, and the permeate feed to downstream processing may be replaced by a permeate tank.

What is claimed is:

1. A carbonylation method, comprising:
    combining epoxide, carbon monoxide, carbonylation catalyst and reaction solvent to produce a product stream comprising beta-lactone, residual epoxide, residual carbon monoxide, carbonylation catalyst, and the reaction solvent;
    contacting the product stream with a membrane separation system, wherein the membrane separation system comprises a membrane having a permeate side and a retentate side, and wherein the product stream is contacted with the membrane separation system on the retentate side of the membrane;
    contacting the membrane separation system with a sweep stream on the permeate side of the membrane, wherein the sweep stream comprises solvent saturated with one or more components of a feed stream, whereby the sweep stream minimizes flux of the one or more components across the membrane;
    outputting a permeate stream on the permeate side of the membrane, wherein the permeate stream is formed when at least a portion of the feed stream crosses the membrane and joins with the sweep stream, wherein the permeate stream comprises beta-lactone; and
    retaining a retentate stream on the retentate side of the membrane, wherein the retentate stream is formed from the remaining feed stream after at least a portion of the feed stream crosses the membrane, wherein the retentate stream comprises carbonylation catalyst and carbon monoxide.

2. The method of claim 1, wherein the sweep stream is a counter-current stream, the feed stream passes tangentially along the surface of the membrane, or both.

3. The method of claim 1, wherein the one or more components in the sweep stream is carbon monoxide, and the sweep stream minimizes flux of carbon monoxide across the membrane.

4. The method of claim 1, wherein the feed stream contacts the membrane separation system at a feed stream pressure, and
    wherein the sweep stream contacts the membrane separation system at a sweep stream pressure, and
    wherein the sweep stream pressure is equal to or lower than the feed stream pressure.

5. The method of claim 1, wherein the membrane separation system has a transmembrane pressure of between 30 bar and 40 bar, and the membrane separation system operates at a constant average temperature.

6. The method of claim 1, comprising driving flux of the beta-lactone from the feed stream to the permeate stream by introducing a concentration of beta-lactone in the feed stream that is higher than the concentration of beta-lactone in the sweep stream.

7. The method of claim 1, wherein the retentate stream further comprises reaction solvent, carbon monoxide, epoxide or beta-lactone, or any combination thereof.

8. The method of claim 1, wherein the membrane separation system is a plate-and-frame membrane system, a hollow fiber membrane system, or a spiral membrane system.

9. The method of claim 2, wherein the one or more components in the sweep stream is carbon monoxide, and the sweep stream minimizes flux of carbon monoxide across the membrane.

10. The method of claim 3, wherein the feed stream contacts the membrane separation system at a feed stream pressure, and
    wherein the sweep stream contacts the membrane separation system at a sweep stream pressure, and
    wherein the sweep stream pressure is equal to or lower than the feed stream pressure.

11. The method of claim 4, wherein the membrane separation system has a transmembrane pressure of between 30 bar and 40 bar, and the membrane separation system operates at a constant average temperature.

* * * * *